United States Patent [19]
Busin et al.

[11] Patent Number: 5,534,560
[45] Date of Patent: Jul. 9, 1996

[54] COMPOUND FOR THE CORRECT TAKING OF DENTAL IMPRESSIONS

[75] Inventors: Tiziano Busin; Enrico Faccio, both of Badia Polesine, Italy

[73] Assignee: Zhermack S.p.A., Badia Polesine, Italy

[21] Appl. No.: 30,976

[22] Filed: Mar. 12, 1993

[30] Foreign Application Priority Data

Mar. 18, 1992 [IT] Italy .................... PD92A0043

[51] Int. Cl.$^6$ .............. A61K 6/10; A61C 9/00; C08K 5/24; C08K 5/05
[52] U.S. Cl. .................. 523/109; 433/214; 524/261; 524/268; 524/379
[58] Field of Search .................. 523/109; 433/214; 524/261, 268, 379; 424/435

[56] References Cited

U.S. PATENT DOCUMENTS

| | | | |
|---|---|---|---|
| 4,389,496 | 6/1983 | Leüsner et al. | 523/109 |
| 4,609,687 | 9/1986 | Schwabe et al. | 523/109 |
| 4,778,832 | 10/1988 | Futami et al. | 523/109 |
| 4,837,261 | 6/1989 | Hampe et al. | 524/268 |
| 4,963,347 | 10/1990 | Humphries et al. | 424/49 |
| 4,992,256 | 2/1991 | Skaggs et al. | 424/7.1 |
| 5,064,891 | 11/1991 | Fujiki et al. | 523/109 |

FOREIGN PATENT DOCUMENTS

| | | |
|---|---|---|
| 0231420 | 8/1987 | European Pat. Off. . |
| 2600886 | 1/1988 | France . |
| 8000057 | 1/1980 | WIPO . |
| 8703001 | 5/1987 | WIPO . |

Primary Examiner—Paul R. Michl
Assistant Examiner—LaVonda R. DeWitt
Attorney, Agent, or Firm—Guido Modiano; Albert Josif

[57] ABSTRACT

The compound for the correct taking of dental impressions is in a liquid solution and includes a surface-active substance, compatible with silicone materials, combined with a solvent. A very light color and a flavoring agent are advantageously added.

6 Claims, No Drawings

COMPOUND FOR THE CORRECT TAKING OF DENTAL IMPRESSIONS

BACKGROUND OF THE INVENTION

The present invention relates to a compound for the correct taking of dental impressions.

Dental impressions are currently mainly taken using silicone materials, which have, with respect to other materials, characteristics of good accuracy, easy handling and are odorless and tasteless and can thus be excellently used in the mouth.

However, silicone materials are hydrophobic, and this is a limit due to the presence of saliva in the regions where it is applied.

In order to eliminate this drawback, some dentist surgeries use cleansing solutions to be sprayed on the stumps before taking the impressions to prevent the possible presence of moisture from causing the forming of bubbles and pores on the impressions which would reduce their accuracy.

Again to solve the drawback due to the fact that silicone materials are hydrophobic, a compound has been devised constituted by a silicone and by a surface-active substance (so as to make the silicone water-compatible).

This compound is used directly to take the impressions without preliminary cleansing.

However, this has produced other drawbacks due to the fact that the surface-active substance increases the viscosity of the silicone and thus makes it more difficult to handle and shortens its life, i.e. the period within which the silicone can be used starting from the time of its preparation.

Furthermore, the effectiveness of the surface-active substance is not very high.

SUMMARY OF THE INVENTION

An aim of the present invention is to provide a compound to be applied on the regions being treated prior to the taking of dental impressions with silicone materials, which eliminates the drawbacks described above in the known art.

Another objective of the present invention is to replace the compounds currently in use with mere cleansing functions.

Another important objective is to provide a compound the presence of which improves the accuracy characteristics of the impressions without worsening the intrinsic characteristics of the silicone materials used.

Another objective is to provide a compound which can be obtained with easily available components.

Another objective is to provide a compound which can be produced at low cost.

This aim, these objects and others which will become apparent hereinafter are achieved by a compound for the correct taking of dental impressions, characterized in that it comprises a surface-active substance, compatible with silicone materials, combined with a solvent.

Further characteristics and advantages of the present invention will become apparent from the following description of a preferred composition thereof, given merely by way of non-limitative example.

BRIEF DESCRIPTION OF THE PREFERRED EMBODIMENTS

The compound according to the present invention is in a liquid solution which can be nebulized and is thus suitable to be sprayed onto the regions affected by impression taking, and comprises a surface-active substance which is compatible with silicone materials, for example constituted by a silicone-glycol-copolymer, combined with a solvent, for example volatile silicone oil or ethyl alcohol.

To these components it is advantageously possible to add a very light color, and/or a flavoring agent, for example sage and mint.

Advantageously, the preferred composition is as follows:

silicone-glycol-copolymer: approximately 98% volatile silicone oil: approximately 2% flavoring agent: sufficient quantity coloring agent: sufficient quantity.

This compound, applied prior to taking the impressions, changes the silicone material from hydrophobic to water-compatible only in the region of contact with the stump the impression of which is to be taken.

The solvent used has the purpose of allowing rapid expansion of the surface-active substance over the entire region of application and of allowing the entire solution to be nebulized.

In this manner the structure of the silicone material is not altered in any way; the material can thus be produced without reducing its life, increasing its viscosity or changing its other characteristics.

It should also be stressed that the use of the compound considerably increases the effectiveness of the silicone material in taking the impressions.

In practice it has been observed that the intended aim and objectives of the present invention have been achieved.

The invention thus conceived is susceptible to numerous modifications and variations, all of which are within the scope of the inventive concept.

All the details may furthermore be replaced with other technically equivalent elements.

We claim:

1. Nebulizable liquid composition for application on surfaces to be affected by dental impression taking before applying thereon dental impression silicone materials, wherein the liquid composition comprises a surface-active substance, a solvent for said surface-active substance, a coloring agent and a flavoring agent, and wherein the surface-active substance is a silicone-glycol copolymer compatible with silicone materials.

2. Composition according to claim 1, wherein said flavoring agent is sage and mint.

3. Nebulizable liquid composition for application on surfaces to be affected by dental impression taking before applying thereon dental impression silicone materials, wherein the liquid composition comprises a surface-active substance, a solvent for said surface-active substance and a flavoring agent, the surface-active substance being a silicone-glycol copolymer compatible with silicone materials, said flavoring agent being selected from the group consisting in sage and mint, wherein said silicone-glycol-copolymer is around 2%.

4. Method for taking dental impressions comprising a step of applying on a surface to be affected by impression taking, before applying thereon dental impression silicone materials, a nebulizable liquid composition, said composition comprising a surface-active substance, a solvent for said surface-active substance, a coloring agent and a flavoring agent, wherein the surface-active substance is a silicone-glycol copolymer compatible with silicone materials.

5. Nebulizable liquid composition for application on surfaces to be affected by dental impression taking before applying thereon dental impression silicone materials, wherein the liquid composition comprises a surface-active substance, a solvent for said surface-active substance and a flavoring agent, the surface-active substance being a silicone-glycol copolymer compatible with silicone materials and said flavoring agent being selected from the group consisting of sage and mint.

6. Method for taking dental impressions comprising a step of applying on a surface to be affected by impression taking, before applying thereon dental impression silicone materials, a nebulizable liquid composition, said composition comprising a surface-active substance, a solvent for said surface-active substance and a flavoring agent, wherein the surface-active substance is a silicone-glycol copolymer compatible with silicone materials and said flavoring agent is selected from the group consisting of sage and mint.

* * * * *